United States Patent [19]
Ehrenfels et al.

[11] Patent Number: 5,836,503
[45] Date of Patent: Nov. 17, 1998

[54] INSERTION DEVICE FOR SURGICAL APPARATUS

[75] Inventors: Karl H. Ehrenfels, Ridgefield, Conn.; Robert H. Schnut, Carmel, N.Y.

[73] Assignee: United States Surgical Corporation, Norwalk, Conn.

[21] Appl. No.: 636,104

[22] Filed: Apr. 22, 1996

[51] Int. Cl.⁶ ...................................................... A61B 17/68
[52] U.S. Cl. ...................... 227/175.1; 227/19; 227/178.1; 227/179.1
[58] Field of Search .............................. 227/175.1, 175.2, 227/176.1, 178.1, 179.1, 180.1, 19

[56] References Cited

U.S. PATENT DOCUMENTS

| | | |
|---|---|---|
| 681,387 | 8/1901 | Bohlig . |
| 832,201 | 10/1906 | Kistler . |
| 1,796,072 | 3/1931 | Baer . |
| 2,067,031 | 1/1937 | Wappler . |
| 2,204,275 | 6/1940 | Kesling . |
| 2,485,939 | 10/1949 | Tedford . |
| 2,924,218 | 2/1960 | Walden et al. . |
| 3,495,586 | 2/1970 | Regenbogen . |
| 3,506,011 | 4/1970 | Silverman . |
| 3,517,128 | 6/1970 | Hines . |
| 3,789,847 | 2/1974 | Lehmann . |
| 3,826,242 | 7/1974 | Eggers . |
| 3,882,852 | 5/1975 | Sinnreich . |
| 4,195,624 | 4/1980 | Douglas . |
| 4,198,982 | 4/1980 | Fortner et al. . |
| 4,207,898 | 6/1980 | Becht . |
| 4,263,914 | 4/1981 | Pawlak . |
| 4,304,236 | 12/1981 | Conta et al. . |
| 4,471,782 | 9/1984 | Shuffield . |
| 4,505,272 | 3/1985 | Utyamyshev et al. . |
| 4,583,542 | 4/1986 | Boyd . |
| 4,585,437 | 4/1986 | Simms . |
| 4,592,354 | 6/1986 | Rothfuss . |
| 4,700,703 | 10/1987 | Resnick et al. . |
| 4,712,536 | 12/1987 | Hawks . |
| 4,817,847 | 4/1989 | Redtenbacher et al. . |
| 4,873,977 | 10/1989 | Avant et al. . |
| 4,957,486 | 9/1990 | Davis . |
| 5,078,720 | 1/1992 | Burton et al. . |
| 5,104,025 | 4/1992 | Main et al. . |
| 5,119,983 | 6/1992 | Green et al. . |
| 5,139,513 | 8/1992 | Segato . |
| 5,176,127 | 1/1993 | Dormia . |
| 5,197,648 | 3/1993 | Gingold . |
| 5,197,649 | 3/1993 | Bessler et al. . |
| 5,205,459 | 4/1993 | Brinkerhoff et al. ...................... 227/19 |
| 5,222,963 | 6/1993 | Brinkeroff et al. . |
| 5,275,322 | 1/1994 | Brinkerhoff et al. . |
| 5,309,927 | 5/1994 | Welch . |
| 5,314,436 | 5/1994 | Wilk . |
| 5,344,426 | 9/1994 | Lau et al. . |
| 5,355,897 | 10/1994 | Pietrafitta et al. . |
| 5,404,870 | 4/1995 | Brinkerhoff et al. . |
| 5,445,644 | 8/1995 | Pietrafitta et al. . |

FOREIGN PATENT DOCUMENTS

| | | |
|---|---|---|
| 3300768 | 4/1985 | Germany . |
| 9006085 | 6/1990 | WIPO . |

OTHER PUBLICATIONS

Article entitled "An Old Head on New Shoulders" by Badger and Allan, Published in the International Journal of Colorectal Disease; pp. 215–216; 1994.

*Primary Examiner*—Scott A. Smith

[57] ABSTRACT

An insertion device is provided for use with surgical tissue fastening apparatus. The insertion device includes a head having an atraumatic leading surface and a shaft extending proximally therefrom. The shaft includes attachment structure for detachable engagement with surgical tissue fastening apparatus. The atraumatic leading structure aids in insertion of the surgical apparatus during a stapling procedure. The shaft, in combination with the head, can also be dimensioned and configured to prevent activation of a surgical tissue fastening apparatus while installed thereon. The insertion device can also include structure to protect and retain fasteners contained within the surgical tissue fastening apparatus. Further, the disclosed insertion devices can be constructed so as to reduce overall weight and alleviate suction effects associated with insertion and retraction.

23 Claims, 5 Drawing Sheets

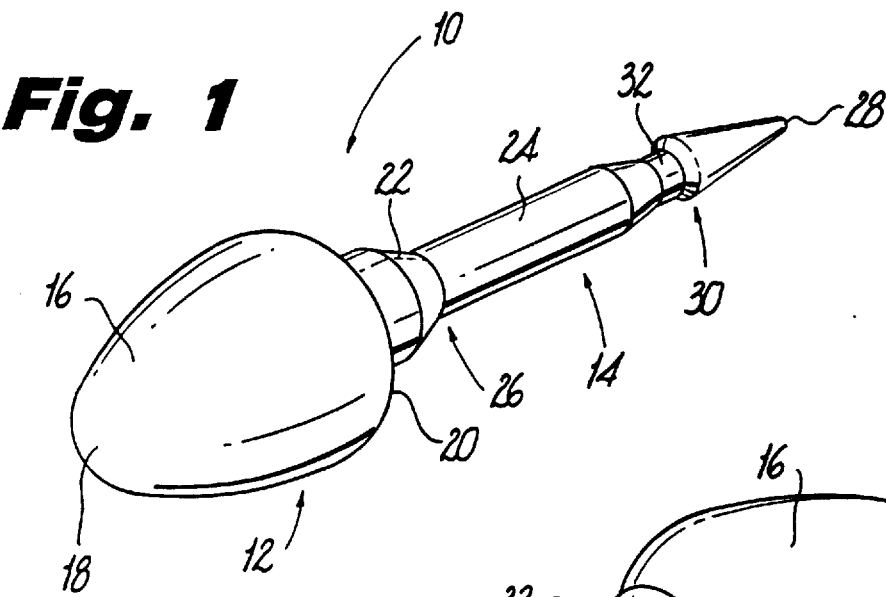
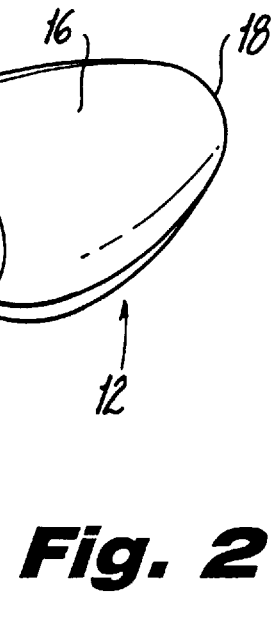
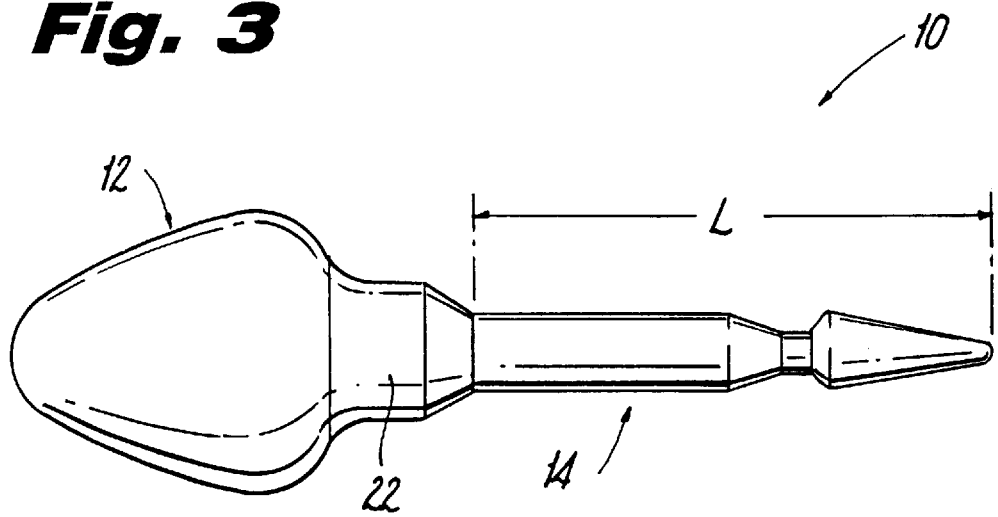

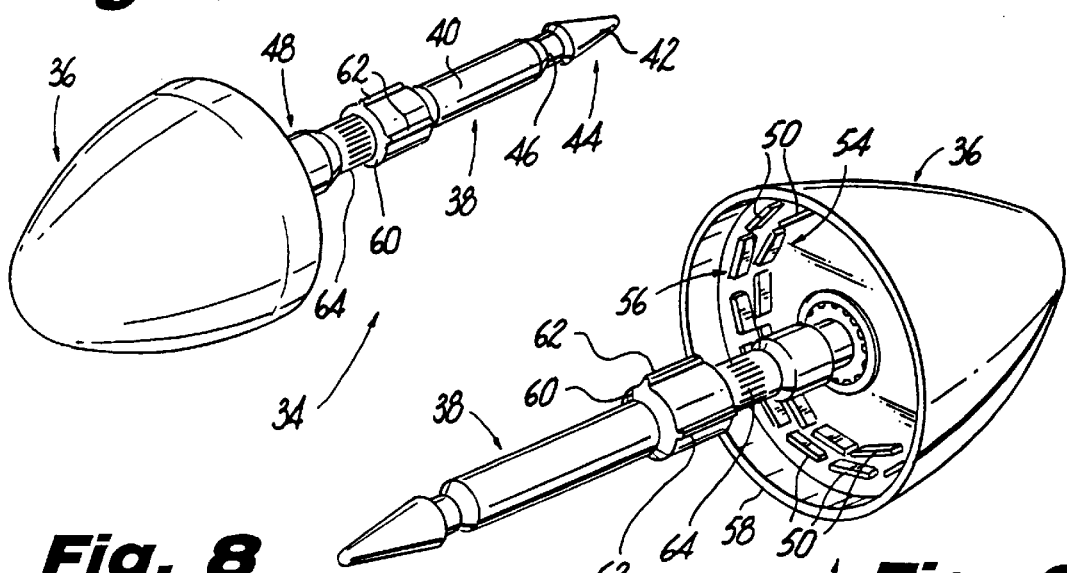
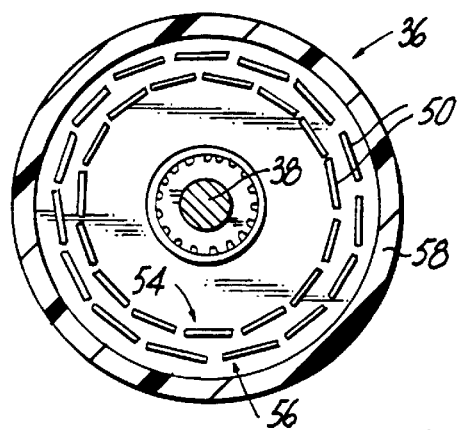
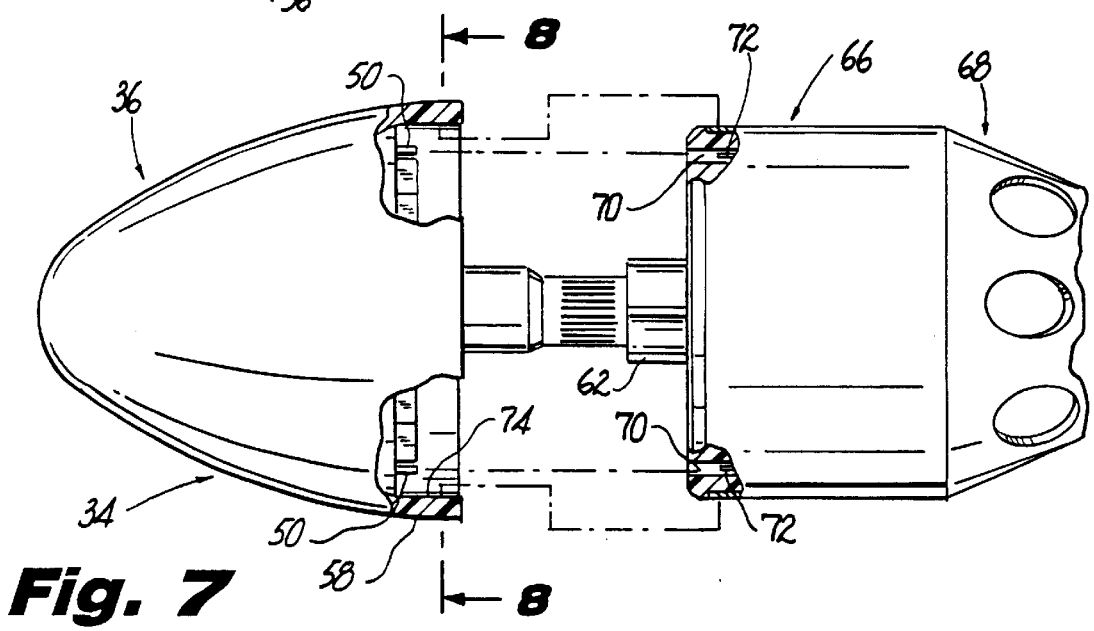

INSERTION DEVICE FOR SURGICAL APPARATUS

BACKGROUND

1. Technical Field

The technical field relates generally to surgical instruments and, more particularly, to an insertion device for use with a surgical tissue fastening apparatus.

2. Description of Related Art

During certain surgical procedures, it is often necessary to insert one or more surgical instruments into a body cavity through a natural opening or orifice. For example, in surgical procedures involving hollow organ tissue sections, such as colon surgery, it is often necessary to remove a diseased or damaged hollow organ tissue section and insert a surgical apparatus trans-anally in order to reconnect the healthy tissue sections.

In one known method of reconnecting the healthy tissue sections, a surgical tissue fastening apparatus such as a surgical stapler or multi-part surgical fastening device having a staple clinching anvil or corresponding component of a multipart fastener installed on a distal end thereof is inserted trans-anally. See, for example, U.S. Pat. No. 5,119,983, the contents of which is incorporated by reference. The staple clinching anvil, or corresponding component of a multi-part surgical fastener, is inserted through the colon, past the diseased tissue section and prepositioned within the healthy distal colon section. The anvil or multipart fastener is disconnected from the tissue fastening apparatus and the tissue fastening apparatus is removed from the body. The diseased section of tissue is excised and removed from the operative site and the surgical tissue fastening apparatus is reinserted through the rectal stump up to the distal colon section. The shaft of the anvil or multipart fastener is then reconnected to a center rod of a surgical tissue fastening apparatus and the center rod is retracted to approximate the anvil towards the fastener cartridge of the surgical tissue fastening apparatus thus bringing the healthy ends of the distal colon tissue section and rectal stump into abutment for fastening. The surgical stapler or surgical fastening apparatus is then activated to staple or otherwise fasten the rectal stump to the distal colon tissue section and the surgical tissue fastening apparatus is thereafter removed trans-anally.

In certain tissue fastening instruments, such as that disclosed in U.S. Pat. No. 5,005,749, the contents of which is incorporated herein by reference, a safety mechanism is provided to prevent activation of the fastening apparatus i.e., ejection of staples or compression assembly of multipart fastener components, prior to minimal approximation of the anvil or fasteners to the fastener cartridge of the apparatus. Upon sufficient retraction of the center rod and anvil or fasteners the minimum distance, the safety mechanism is disabled and the surgical tissue fastening apparatus can be fired. As disclosed in U.S. Pat. No. 5,005,749, should, for example, the anvil, and thus the center rod, be retracted less than the predetermined minimal distance, the safety mechanism will remain enabled and prevent activation of the instrument.

One recent article has suggested that, to facilitate re-insertion of the stapling apparatus after placement of the anvil, an old, used stapling anvil can be attached to the stapling apparatus so as to provide a blunt surface as the stapling apparatus is advanced through the rectal stump. While providing a smooth surface over the staple cartridge may ease insertion, the use of an anvil, particularly one not originally provided with the stapler, is not advisable. For example, despite attempts to sterilize a used anvil, the potential inherent risks and danger of cross-contamination by this proposed procedure are apparent. In addition, if an anvil other than one supplied with the surgical stapler is mistakenly used to clinch the staples during the procedure, there is a risk that the staples will become malformed. Also, insertion of the stapler with an anvil closely approximated after already placing the original anvil in the body may result in an inadvertent firing of the stapler.

An alternative method and device for inserting a surgical stapler part way into the rectal stump trans-anally is disclosed in U.S. Pat. No. 5,404,870 and includes a sheath open at both ends and having members which retain the sheath near the rectal opening. The surgical stapler is inserted through the sheath and out the distal end thereof. While the device disclosed in U.S. Pat. No. 5,404,870 may, to a limited extent, aid in inserting a surgical stapler through the rectal opening, the device is of a fixed length and may not extend sufficiently far into the rectal stump to shield the surgical stapler as it is advanced to the operative site. Additionally, the device remains positioned within the rectal stump during the entire surgical procedure and may be a source of irritation and/or a nuisance to the surgeon.

Thus, there is a need for a safe and efficient insertion device to facilitate entry and movement of a surgical tissue fastening apparatus trans-anally through and up to the desired surgical site.

SUMMARY

An insertion device is provided to facilitate atraumatic insertion of a surgical instrument into and through a body orifice. In a preferred embodiment, the insertion device includes a head having an atraumatic leading surface and a shaft extending from the head. The head is anvilless and thus devoid of staple clinching structure. The shaft can be formed separately or molded integrally with the head. The head preferably has a diameter substantially equal to or greater than the maximum diameter of a distal end of the surgical tissue fastening apparatus used therewith. The head shaft can be solid and insertable into a tubular center rod of the surgical staple (see, for example, U.S. Pat. No. 5,119,983) or the shaft can be hollow and slidable over a solid center rod of the surgical staple (see, for example, U.S. Pat. No. 5,205,459). In either case, either the shaft and/or instrument center rod is provided with attachment structure for attachment to the surgical stapler. Preferably, the attachment structure is a circumferential groove adjacent an end of the solid structure.

The disclosed insertion devices can also provide a lockout function when used with surgical tissue fastening apparatus incorporating retraction based safety mechanisms. These mechanisms require that a center rod be retracted a predetermined minimal distance before the apparatus can be fired. The shaft of the insertion device is dimensioned and configured such that the head of the insertion device will contact the fastener cartridge at the distal end of the apparatus prior to retraction sufficient for firing.

In another preferred embodiment of the insertion device, the anvilless head is provided with structure to protect and retain staples contained within staple pockets of a surgical stapler. The structure can include projections, preferably arranged in concentric rings, each of which extend into a corresponding staple pocket of the surgical stapler to protect and retain the staple therein. Preferably, the shaft is provided with alignment structure in the form of a plurality of longitudinal ribs. The ribs engage corresponding structure on the surgical tissue fastening apparatus and ensures proper alignment of each of the projections within a corresponding staple pocket. Additionally, a circumferential flange can be provided that extends proximally from the head to overlap the distal end of the surgical tissue fastening apparatus thereby further shielding the staple cartridge.

In another preferred embodiment, the anvilless insertion device can have one or more recesses disposed therein to reduce weight and help prevent undesired suction effects.

BRIEF DESCRIPTION OF THE DRAWINGS

Various embodiments are described herein with reference to the drawings, wherein:

FIG. 1 is a perspective view seen from the distal end to the proximal end of one embodiment of an insertion device;

FIG. 2 is perspective view seen from the proximal end to the distal end of the insertion device of FIG. 1;

FIG. 3 is a side elevational view of the insertion device of FIG. 1;

FIG. 5 is a perspective view seen from the distal end to the proximal end of another embodiment of an insertion device;

FIG. 6 is a perspective view seen from the proximal end to the distal end of the insertion device of FIG. 5 illustrating a proximal face of the insertion device;

FIG. 7 is a side elevational view, partially shown in section, of the insertion device of FIG. 5 inserted into the distal end of a surgical stapling apparatus;

FIG. 8 is a sectional view taken along line 8—8 of FIG. 7;

DETAILED DESCRIPTION OF PREFERRED EMBODIMENTS

Figure 4:
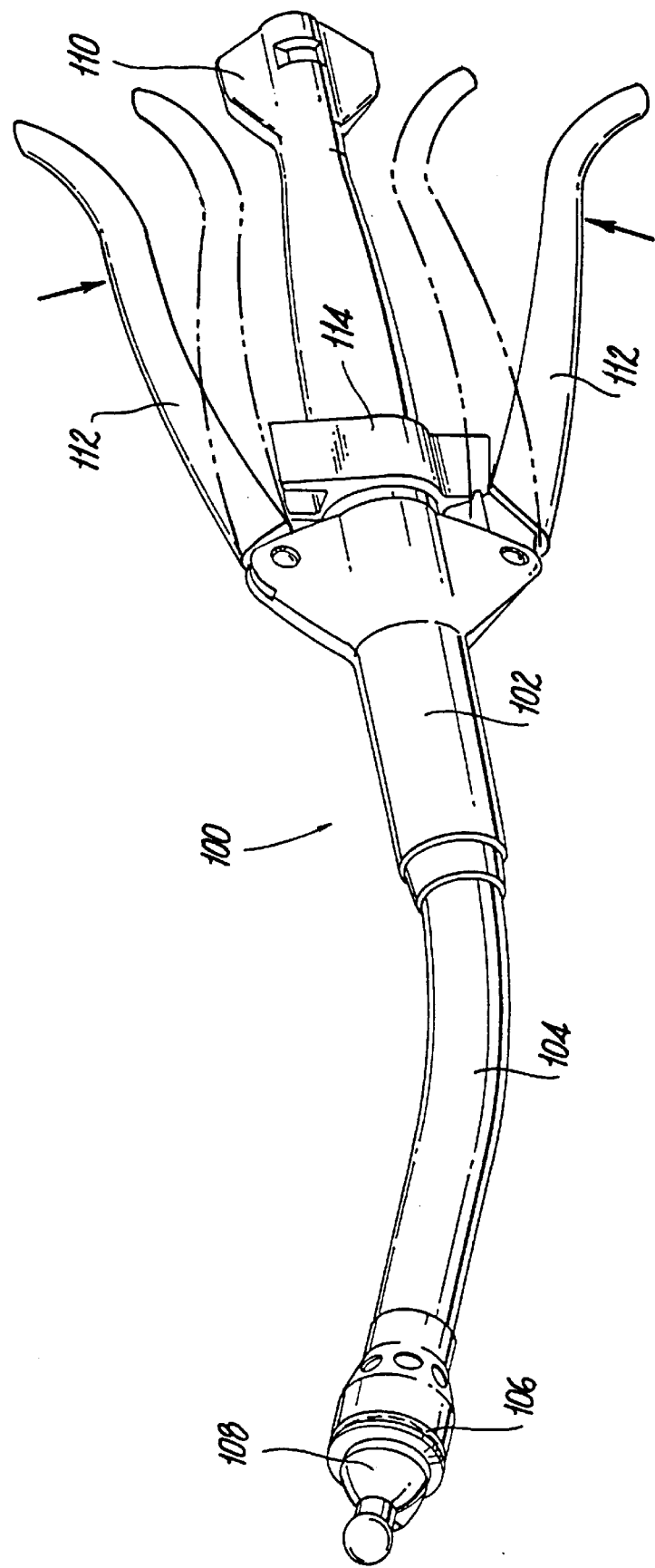
FIG. 4 is a perspective view of an anastomosis surgical stapling instrument for use with the several embodiments of the insertion device.

Referring now to FIGS. 1–3, and initially to FIGS. 1 and 2, there is shown an insertion device 10 for use with surgical tissue fastening apparatus such as those disclosed in, for example, U.S. Pat. Nos. 5,005,749 and 5,119,983, the entire disclosures of which are incorporated by reference herein. While the following discussion of the various embodiments of the insertion device is given with respect to a circular surgical stapler in general and, in particular, an anastomosis surgical stapling instrument such as that disclosed in U.S. Pat. No. 5,005,749, it will be noted that the insertion device is equally applicable for use with multipart surgical fastening devices such as a fragmentable anastomosis ring applier disclosed in U.S. Pat. No. 5,376,098 or the like. As used herein the term "distal" refers to that part of the device, or component thereof, furthest from the user, while the term "proximal" refers to that part of the device, or component thereof, closer to the user.

Insertion device 10 is designed to provide a smooth leading surface for trans-anal insertion of the surgical tissue fastening apparatus and generally includes head 12 and a shaft 14 extending proximally therefrom. Head 12 is monolithically formed and has a smooth atraumatic leading or outer surface 16. Preferably, head 12 has a rounded distal end 18 and relatively rounded off proximal end 20 adjacent shaft 14. Both head 12 and shaft 14 are preferably fabricated from a biocompatible material.

A head extension 22 is preferably provided intermediate proximal end 20 and shaft 14 to provide a smooth transition therebetween. It should be noted that both head 12 and head extension 22 are anvilless, that is, devoid of any staple clinching structure such as, for example, a ring of staple clinching buckets. Shaft 14 generally includes a shaft barrel 24, a distal end 26 of which is inserted and affixed within a bore of head 12 and/or head extension 22. Alternatively, shaft 14 and head 12 can be integrally formed or molded. Shaft 14 preferably includes a conical tip 28 formed on a proximal end 30 of shaft barrel 24. Alternatively, the shaft can be hollow as discussed in greater detail with respect to FIG. 12.

In order to facilitate attachment of insertion device 10 to a surgical tissue fastening apparatus, attachment structure, preferably in the form of a radial recess or groove 32, is formed in shaft barrel 24 at proximal end 30 thereof and adjacent conical tip 28. Groove 32 is dimensioned and configured for detachable engagement with corresponding retaining structure, such as that contained in a distal end of a center rod, provided in the surgical stapling instrument (not shown).

As noted above, head 12 is preferably formed as a solid monolithic structure. Preferably head 12 has a maximum radius substantially equal to the maximum radius of a distal end of the surgical stapling instrument. Head 12 can be formed by various methods, such as, injection molding of a suitable biocompatible plastic, for example. Additionally, shaft 14 can be molded integrally with head 10 or can be formed as a separate structure.

When shaft 14 is formed separately, it is preferably formed of stainless steel or plastic. Head 12 and shaft 14 can be assembled by inserting distal end 26 of shaft 14 in a bore of head 12 and/or head extension 22. Shaft 14 can be secured to head 12 and/or head extension by various means, such as, for example, a threaded interconnection or securing distal end 26 within the bore by means of a suitable adhesive.

As noted above, insertion device 10 is particularly designed for use with surgical tissue fastening apparatus employing a retraction dependent safety mechanism, such as, for example, the anastomosis surgical stapling instrument disclosed in U.S. Pat. Nos. 5,005,749 and 5,119,983. A retraction dependent safety mechanism disables or blocks activation of the stapling instrument until such time as a center rod, having a staple clinching anvil affixed thereto, has been retracted to within a minimal predetermined distance from the staple cartridge disposed at the distal end of the stapling instrument. This predetermined distance ensures that the specific size staple will completely penetrate the tissue sections to be fastened and will be properly crimped by the staple clinching buckets of the anvil thereby preventing incomplete stapling of the tissue sections. Thus, it is the center rod that must move the predetermined minimal distance before the safety mechanism is disabled.

The disclosed insertion devices and, in particular, insertion device 10 prevents firing when installed on the stapling instrument. Referring now to FIG. 3, this is accomplished by configuring and dimensioning the length "L" of shaft 14 so that the center rod cannot be retracted to within the predetermined minimal distance required for firing. Preferably, head 12 and/or head extension 22 abut a distal end of the surgical stapling instrument before the predetermined minimal distance is achieved. Thus the surgical stapling instrument cannot be activated while insertion device 10 is installed thereon.

Referring to FIG. 4, there is shown an anastomosis surgical stapling instrument such as that disclosed in U.S. Pat. No. 5,005,749. The instrument 100 includes a yoke 102, a pusher tube assembly 104 which extends from the yoke 102 to carry a staple assembly 106 at the distal end, an anvil assembly 108 at the distal end of the instrument and an actuating mechanism which extends from the anvil assembly 108 through the pusher tube assembly 104 to a wing nut 110 at the proximal end of the instrument for moving the anvil assembly 108 relative to the pusher tube assembly 106. In addition, a pair of handles 112 are pivotally mounted on the yoke 102. Handles 112 are mounted so as to be manually grasped by a surgeon and moved towards each other, as indicated by the arrows in order to fire the staples (not shown) from the staple assembly 106 towards the anvil assembly 108. A safety lock 114 is also mounted on the proximal end of the yoke 102. Safety lock 114 is blocked from rotating out of the way of handles 112 until a center rod has been retracted a predetermined minimal distance in the manner disclosed in U.S. Pat. No. 5,005,749.

Referring now to FIGS. 5–8, and initially to FIGS. 5 and 6, there is shown an alternate embodiment of an insertion device which, in addition to performing the activation prevention and atraumatic insertion functions described hereinabove with respect to insertion device 10, is particularly configured to protect and secure staples located in staple pockets of the surgical stapling instrument during insertion of the surgical stapling instrument into and through a body cavity, such as, the rectal stump. Insertion device 34 is similar to insertion device 10 and generally includes a substantially monolithically formed head 36, devoid of staple clinching structure, and a shaft 38 extending from head 36.

Shaft 38 is similar to shaft 14 described above and includes a shaft barrel 40 preferably having a conical tip 42 at a proximal end 44 thereof. Attachment structure in the form of a radial recess or groove 46 is formed in the proximal end 44 of shaft barrel 40 to facilitate detachable engagement of insertion device 34 with a suitable surgical tissue fastening device in the manner described hereinabove with respect to insertion device 10. A distal end 48 of shaft 38 is affixed within head 36, or integrally molded therewith, in the manner described hereinabove with respect to insertion device 10.

Insertion device 34 is specifically configured to protect and retain staples within staple pockets of a surgical stapler during insertion of the stapler into and through a body cavity. Thus, as best shown in FIGS. 6 and 8, head 36 includes a plurality of proximally facing projections 50 extending from a proximal face 52 of head 36. Preferably, projections 50 are arranged in two staggered and concentric rings such as, for example, inner and outer rings 54 and 56, respectively.

Inner and outer rings 54 and 56 are arranged so as to position a single projection 50 within a single staple containing pocket of a surgical stapling instrument upon retraction of insertion device 34 adjacent the staple cartridge at the distal end of a stapling instrument as will be described in more detail below.

Head 36 also includes a circumferential and proximally extending flange 58 which is configured to overlap an outer edge of the distal end of an associated surgical stapling instrument. Flange 58 inhibits debris and fluids from entering the space between insertion device 34 and the distal end of the stapling instrument and also provides for a smooth transition between the insertion device and stapler.

Referring to FIGS. 5 and 6, in order to aid in aligning projections 50 with corresponding staple pockets, shaft 38 includes alignment structure in the form of an alignment sleeve 60 having a plurality of circumferentially spaced ribs 62. Sleeve 60 may be formed integrally with shaft 38 or separately, and secured to shaft 38 by a suitable medical grade adhesive. Ribs 62 are configured to engage corresponding alignment structure within a surgical stapler and thus ensure correct alignment of projections 50 with corresponding individual staple pockets upon retraction. Similar alignment structure is disclosed in U.S. Pat. No. 5,119,983.

Shaft 38 is preferably also provided with a high friction or knurled portion 64 to facilitate grasping insertion device 34 using known surgical grasping instrumentation and techniques.

Referring now to FIG. 7, insertion device 34 is illustrated partially installed in a distal end 66 of a surgical stapling instrument 68. Surgical stapling instrument 68 includes a plurality of circumferentially spaced staple pockets 70 in distal end 66 thereof. Prior to stapling a tissue section, each staple pocket 70 contains a generally U-shaped staple 72 which, when driven out of staple pockets 70, through tissue sections and into a staple clinching anvil member, securely fastens tissue sections together. As shown, an inner surface 74 of flange 58 is dimensioned and configured to overlap an outer circumferential surface of distal end 66. Thus projections 50, in combination with flange 58, protect and retain staples 72 contained within the surgical stapling instrument 68 when insertion device 34 is retracted adjacent to distal end 66 of stapling instrument 68.

Figure 9:
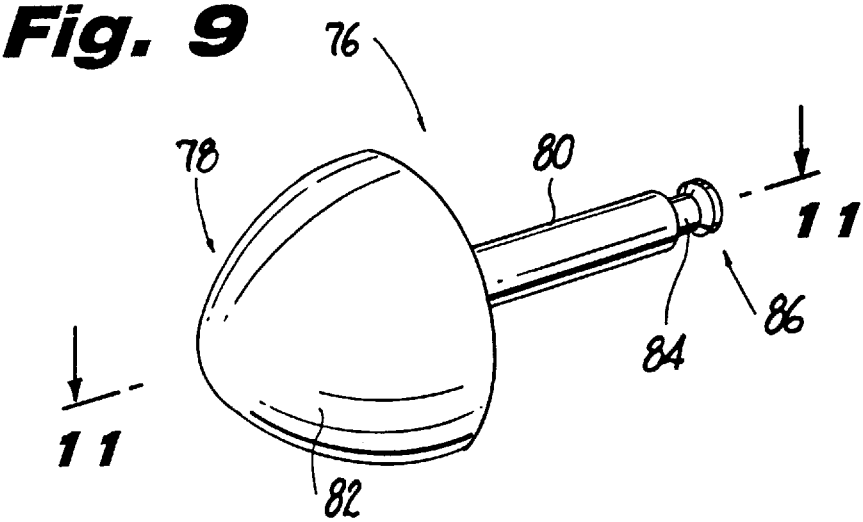
FIG. 9 is a perspective view seen from the distal end to the proximal end of another embodiment of an insertion device.
Figure 10:
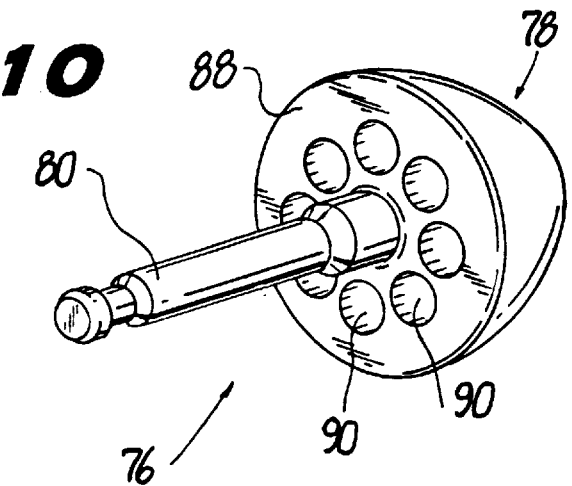
FIG. 10 is a perspective view seen from the proximal end to the distal end of the insertion device of FIG. 9.
Figure 11:
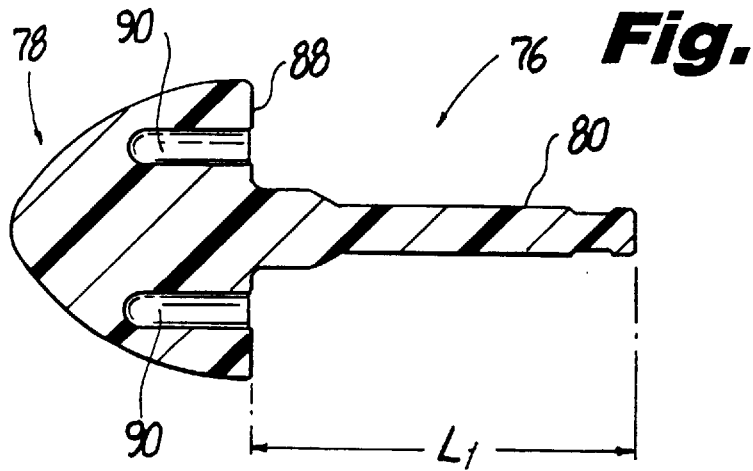
FIG. 11 is a side sectional view taken along line 11—11 of FIG. 9.

Referring now to FIGS. 9–11, and initially to FIG. 9, there is shown another preferred embodiment of an insertion device. Insertion device 76 performs the actuation prevention and atraumatic insertion functions described hereinabove with respect to insertion device 10 and generally includes a head 78, also devoid of staple clinching structure, and a shaft 80 integral with and extending proximally from head 78. Head 78 and shaft 80 are preferably monolithically formed of a suitable material, such as, for example, plastic. Head 78 has a smooth, conical atraumatic leading outer surface 82, while shaft 80 includes attachment structure, preferably in the form of a radial recess or circumferential groove 84, at a distal end 86 thereof.

Referring now to FIGS. 10 and 11, head 78 has a substantially flat proximally facing surface 88 oriented substantially perpendicular to a longitudinal axis of shaft 80. Preferably, head 78 is provided with a plurality of recesses or bores 90 extending from surface 88 partially into head 78. Bores 90 serve to reduce the weight of insertion device 76 as well as reduce suction effects existing between tissue and a surgical tissue fastening device as insertion device 76 is extended and retracted with respect thereto.

Similar to that of insertion device 10, shaft 80 of insertion device 76 is dimensioned and configured to be insertable in the distal end of a surgical stapling instrument. The length "L1" of shaft 80 is also dimensioned and configured such that it prevents deactivation of a safety mechanism when the proximal surface of head 78 is adjacent the distal end of the surgical stapling instrument.

Figure 12:
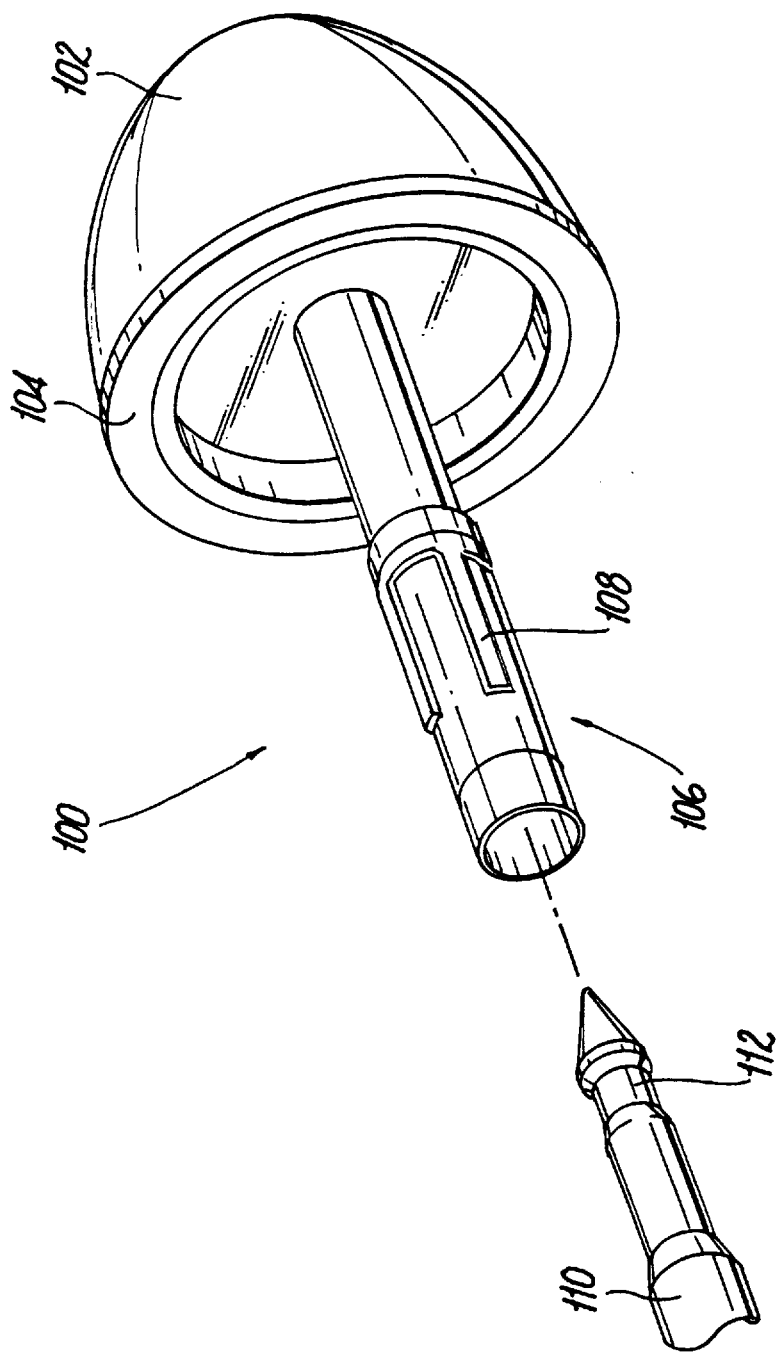
FIG. 12 is a perspective view of an alternate insertion device shaft and corresponding attachment structure from a surgical stapler.

With reference to FIG. 12, an alternate preferred embodiment of an insertion device is shown. Insertion device 100 is similar to the previous embodiments, however, shaft 106 extending from atraumatic head 102 is a hollow structure adapted to receive a solid rod 110 extending from a surgical stapling instrument (not shown). In this embodiment, the insertion device is secured to the stapling apparatus by inserting solid shaft 110 into hollow shaft 106. Solid shaft 110 preferably has circumferential recess 112 which is adapted to engage locking structure associated with the insertion device shaft. Similar shaft connecting structures are disclosed, for example, in U.S. Pat. No. 5,205,459 and can be applied to each previous embodiment disclosed herein. Returning to FIG. 12, the insertion device preferably has a smooth surface 104 devoid of stapling forming pockets and shaft 106 has optional alignment structure 108. As previously described, shaft 106 can be fabricated to have a length sufficient to prevent disengagement of a lockout member which requires a predetermined longitudinal displacement within the stapling apparatus.

It will be understood that various modifications can be made to the embodiments disclosed herein. For example, as noted hereinabove, the disclosed embodiments are suitable for use with various surgical tissue fastening instruments and thus the specific attachment structure can be varied to accommodate the same. Additionally, the various embodiments need not prevent activation of tissue fastening apparatus but can be dimensioned and configured to provide ease of insertion only. Therefore, the above description should not be construed as limiting, but merely as exemplifications of preferred embodiment. Those skilled in the art will envision other modifications within the scope and spirit of the claims appended hereto.

What is claimed is:

1. An insertion device for use with a surgical tissue fastening apparatus comprising:
    a) a shaft configured for engagement with a surgical tissue fastening apparatus; and
    b) a head on a distal end of the shaft, the head having an atraumatic distal surface and an anvilless proximal surface.

2. The insertion device of claim 1, wherein the atraumatic distal surface is an uninterrupted blunt surface.

3. The insertion device of claim 1, wherein the head is formed integrally with the shaft.

4. The insertion device of claim 1, wherein the head is formed by injection molding of a plastic material.

5. The insertion device of claim 1, wherein the shaft is formed of stainless steel.

6. The insertion device of claim 1, wherein the shaft is solid and has attachment structure formed adjacent a proximal end thereof.

7. The insertion device of claim 6, wherein the distance between a proximal end of the head and the attachment structure is sufficiently short to disable a safety mechanism of a surgical tissue fastening apparatus.

8. The insertion device of claim 1, wherein the shaft has a tapered conical tip formed on a proximal end of the shaft.

9. The insertion device of claim 1, wherein the head has an atraumatic and substantially rounded proximal end.

10. The insertion device of claim 1, further comprising a circumferential proximal facing flange extending from a proximal end of the head.

11. The insertion device of claim 10, wherein the flange is configured and dimensioned to overlap a distal end of a surgical tissue fastening apparatus.

12. The insertion device of claim 10, further comprising a plurality of proximally extending projections formed on a proximal end of the head, the projections configured for partial insertion within staple pockets formed in a distal end of a surgical tissue fastening apparatus.

13. The insertion device of claim 12, further comprising alignment structure on the shaft, the alignment structure aligning the projections with the staple pockets.

14. The insertion device of claim 1, wherein the shaft is hollow.

15. The insertion device of claim 14, wherein the hollow shaft is adapted to receive a conical tip formed on a distal end of a rod extending from a surgical instrument.

16. The insertion device of claim 14, wherein the distance between a proximal end of the head and the proximal end of the hollow shaft is sufficiently short to disable a safety mechanism of a surgical tissue fastening apparatus.

17. An anvilless insertion device for use with a surgical tissue fastening apparatus comprising:
    a) a shaft configured for engagement with a surgical tissue fastening apparatus; and
    b) a head on distal end of the shaft.

18. The insertion device of claim 17 wherein a distal portion of the head is conical.

19. The insertion device of claim 17 wherein a proximal end of the head has a substantially flat face.

20. The insertion device of claim 19 wherein the flat face has a radius substantially equal to a radius of distal end of a surgical tissue fastening apparatus used therewith.

21. The insertion device of claim 19 wherein the head includes a plurality of radially spaced recesses extending inwardly into the head.

22. The insertion device of claim 17 wherein the proximal end of the shaft includes attachment structure engageable with corresponding retaining structure of a surgical tissue fastening apparatus.

23. The insertion device of claim 17 wherein the shaft is solid.

* * * * *